United States Patent [19]

Jones et al.

[11] Patent Number: 4,614,194

[45] Date of Patent: Sep. 30, 1986

[54] IMPLANTABLE PULSE GENERATOR HAVING A SINGLE PRINTED CIRCUIT BOARD FOR CARRYING INTEGRATED CIRCUIT CHIPS THEREON WITH CHIP CARRIER MEANS

[75] Inventors: W. Kinzy Jones, Pembroke Pines; Alvin H. Weinberg, Miami, both of Fla.

[73] Assignee: Cordis Corporation, Miami, Fla.

[21] Appl. No.: 572,312

[22] Filed: Jan. 20, 1984

[51] Int. Cl.⁴ .............................................. A61N 1/00
[52] U.S. Cl. .................................. 128/419 P; 357/80; 361/401

[58] Field of Search ....... 128/419 P, 419 PG, 419 PS; 339/17 B, 17 CF, 17 E, 17 LM, 17 M, 17 N; 361/394, 399, 415; 357/72, 74, 80; 29/588, 831, 832, 841; 174/52 FP, 52 PG

[56] References Cited

U.S. PATENT DOCUMENTS

| 4,288,841 | 9/1981 | Gogol | 361/401 |
| 4,399,819 | 8/1983 | Cowdery | 128/419 P |
| 4,445,274 | 5/1984 | Suzuki et al. | 357/80 |

Primary Examiner—William E. Kamm
Attorney, Agent, or Firm—Yount & Tarolli

[57] ABSTRACT

The human implantable pulse generator herein may serve as a cardiac pacer. The housing for the generator is minimized in size by mounting integrated circuit chips, forming the pulse generator circuit, in a hermetically sealed cavity in a chip carrier.

11 Claims, 13 Drawing Figures

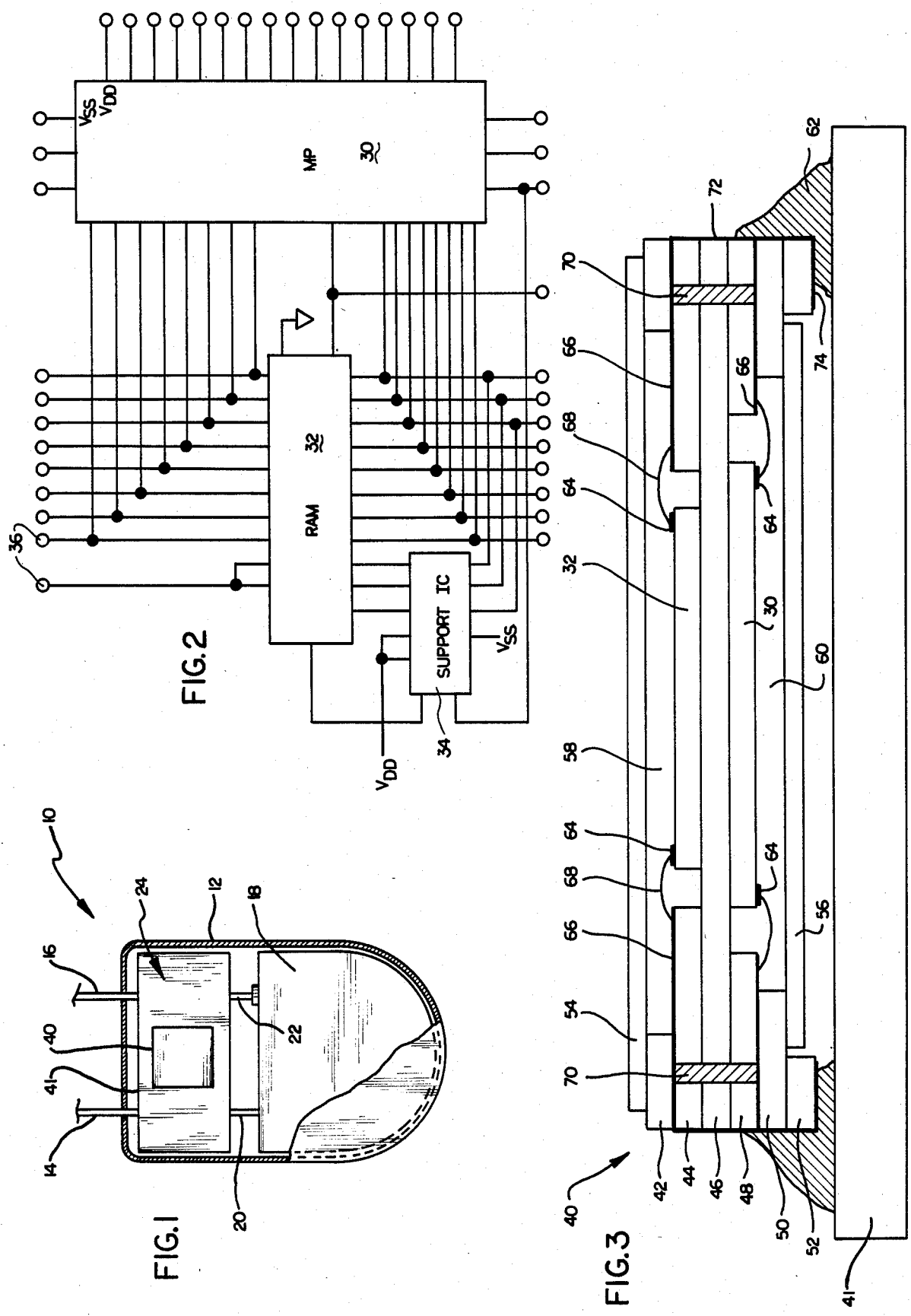

IMPLANTABLE PULSE GENERATOR HAVING A SINGLE PRINTED CIRCUIT BOARD FOR CARRYING INTEGRATED CIRCUIT CHIPS THEREON WITH CHIP CARRIER MEANS

BACKGROUND OF THE INVENTION

This invention relates to improvements directed to implantable pulse generators, such as cardiac pacers, nerve stimulators or a fluid dispenser pump and the like, and will be described with particular reference thereto.

It is known in the art to implant pulse generators within the human body. Such implantable pulse generators include, for example, cardiac pacers, nerve stimulators and fluid dispensing pumps. These pulse generators include a power supply in the form of a battery and a pulse generator circuit all housed in a hermetically sealed housing. The housing may typically take the form of a biocompatible metal case which is sealed so as to be effectively impervious with respect to either gases or liquids. Signals into and out of the circuitry are coupled to the casing by means of feed-through terminals of various types known in the art. An example of such a cardiac pacer may be found in the U.S. patent to A. Ushakoff, U.S. Pat. No. 4,127,134, assigned to the same assignee as the present invention.

From an examination of Ushakoff, supra, it is apparent that the size of the housing is dependent upon that required to house both the battery and the electric circuit, including the pulse generator. The size of the battery depends, to a large extent, upon the anticipated life time, as well as cost factors of the type of battery employed. Improvements have also been made in component packaging and which greatly affect the size of an electric circuit. Thus, the circuitry illustrated in the patent to Ushakoff, supra, shows discrete components as opposed to the integrated circuits or chips as employed in the U.S. patent to A. F. Lesnick, et al., U.S. Pat. No. 4,163,451, also assigned to the assignee herein. The Lesnick patent discloses a microprocessor based pulse generator for use as a cardiac pacer and includes integrated circuits, including active circuits, such as a microprocessor and a random access memory. The use of such integrated circuitry requires less space than discrete components and thus provides a reduction in the size necessary for the circuitry employed in such an implantable pulse generator.

It has been common in the prior art when packaging such electronic circuitry to mount integrated circuits, or IC chips, on a substrate or printed circuit board so that a considerable amount of the surface area thereof was required to mount the various integrated circuits together with interconnections from chip to chip. The recent use of dual in line (DIP) packaging has assisted somewhat in decreasing the size of the contact footprint or square footage area of a substrate used in mounting such chips.

Additional improvements have taken place in electronic packaging that will assist in minimizing the size of an implantable pulse generator. Such improvements include multi-layered ceramic carriers for housing and interconnecting one or more semiconductor integrated circuit chips. An example of such a ceramic carrier is found in the U.S. patent to Gogal, U.S. Pat. No. 4,288,481. This patent discloses a multi-layered ceramic package which is of square shape and is thin in terms of height. A cavity is defined in each of the two major surfaces so as to define a dual cavity chip carrier. Two of the ceramic layers each have a floor surface provided with an enlarged metallized mounting pad for receiving and electrically mounting an integrated circuit chip. Between these two ceramic layers, there is provided metallized patterns, some of which extend to vertical conductive paths or vias which extend to metallized patterns on other ceramic layers and some of the patterns extend to a peripheral edge metallization or castellation. The peripheral or edge castellations extend to a bottom ceramic layer which does not have edge castellations but instead includes vias adjacent its peripheral edges which connect to output contact pads along the bottom surface of the carrier. These contact pads serve as input/output pads so that the carrier may be connected to a motherboard or a substrate.

As noted, the chip carrier disclosed in the Gogal patent, supra, contemplates the use of two ceramic layers intermediate the cavities which individually receive and mount one integrated circuit chip. Additionally, Gogal's structure contemplates that the lowermost layer be void of edge castellations and instead vias extend through the lowermost layer to make contact with an array of input/output contact pads located along the peripheral edges.

SUMMARY OF THE INVENTION

The primary object of the present invention is to provide an improved implantable pulse generator having improvements in electronic packaging of the circuitry involved so as to minimize the size of the casing to be implanted in the human body.

It is a still further object of the present invention to employ improved electronic packaging for an implantable pulse generator wherein the size of the packaging is minimized by utilizing a chip carrier including at least one hermetically sealed cavity in which an integrated circuit is mounted.

It is a still further object of the present invention to provide such an improved implantable pulse generator which includes at least two integrated circuit chips which are hermetically sealed in a chip carrier and wherein the chips are interconnected to each other internally of the chip carrier.

It is a still further object of the present invention to provide such an improved implantable pulse generator employing a dual cavity chip carrier wherein each cavity employs means for receiving and mounting at least one integrated circuit chip in a hermetically sealed cavity.

In accordance with the present invention the implantable pulse generator includes an implantable sealed housing of biocompatible material and which contains a power supply and a pulse generator circuit powered by the supply for providing pulses. The circuit includes at least two integrated semiconductor circuit chips together with a chip carrier for carrying the chips. Semiconductor chips are mounted in a common cavity within one of the major surfaces of the chip carrier and are hermetically sealed therein. These chips are electrically interconnected internally of the carrier. Additionally, a network of metallized paths are located on the various ceramic layers. Some of these metallized paths extend laterally outward to metallized edges which extend vertically along the peripheral edges of the carrier to input/output mounting pads on the bottom surface so that the carrier may be electrically and physically mounted to a motherboard or substrate. A pattern of vertically extending conductive vias interconnect metallized paths located on various different ceramic layers so as to complete electrical circuits therethrough.

In accordance with a still further aspect of the present invention, the implantable pulse generator circuit includes at least three integrated circuit chips and the chip carrier includes two hermetically sealed cavities, one in each major surface thereof with two of the chips being mounted in one of said cavities and the third integrated circuit being mounted in the second cavity so as to thereby minimize the contact area or footprint required for mounting these components on a motherboard or substrate in the implantable pulse generator housing.

BRIEF DESCRIPTION OF THE DRAWINGS

The foregoing and other objects and advantages of the invention will become more readily apparent from the following description of the preferred embodiment of the invention as taken in conjunction with the accompanying drawings which are a part hereof and wherein:

FIG. 1 is a plan view, with parts broken away, of a pulse generator constructed in accordance with the invention;

FIG. 2 is a schematic-block diagram illustration of integrated circuits employed in the pulse generator;

FIG. 3 is an elevational view schematically illustrating the pulse generator circuit of FIG. 2 mounted in a dual cavity chip carrier which is in turn mounted on a substrate;

DESCRIPTION OF THE PREFERRED EMBODIMENT

Figure 4:
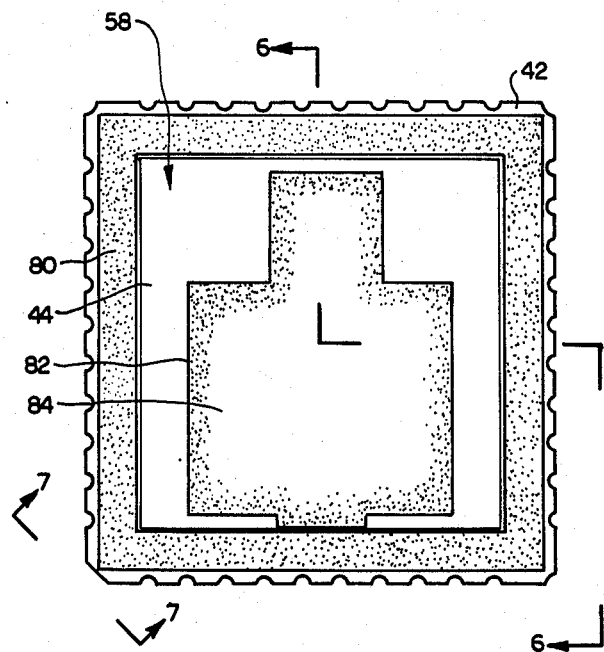
FIG. 4 is a plan view, with the upper lid removed, of the chip carrier.

Reference is now made to the drawings and more particularly to FIG. 1 which illustrates an implantable pulse generator 10 and which takes the form of a cardiac pacer. The pulse generator 10 includes a hermetically sealed housing 12, having a portion of its front face broken away to illustrate the contents therein. The housing 12 is preferably of a human compatible material such as stainless steel or titanium and is designed to be implanted within the human body such that the contents within the casing are hermetically sealed while permitting a pair of electrodes 14 and 16 to extend therefrom. Additionally, the casing includes a battery 18 having cathode and anode terminals 20, 22, respectively, connected to a pulse generator circuit generally designated at 24 so that power is supplied to the pulse generator circuit which in turn provides pulses to the electrodes 14 and 16 for stimulating a heart in a known manner. The pulse generator circuit 24 may take the form, for example, of that illustrated and described in U.S. patent to A. F. Lesnick, et al. U.S. Pat. No. 4,163,451.

As noted in the Lesnick patent, supra, such a pulse generator circuit 24 includes a plurality of integrated circuits. For example, with reference to FIG. 2, this plurality of integrated circuits may include a 40 pin microprocessor 30, a 24 pin random access memory (RAM) 32 and a 16 pin supporting IC chip 34, all interconnected as is illustrated in FIG. 2. It is to be noted in this instance that only 39 of the 40 pins of the microprocessor 30 are employed in this application, all of the 24 pins of memory 32 are employed, and 11 of the 16 pins of the supporting IC chip 34 are employed. Consequently, 74 pins or input/output contact pads of these three integrated circuit chips are employed in this application. If these integrated circuits are to be mounted on a printed circuit board or the like, then substantial wiring is required to make the interconnections. Additionally, the contact area or footprint required is dependent upon the physical size of the integrated circuits and the required spacing between them.

In accordance with the present invention, these integrated circuits are mounted in a single dual cavity chip carrier which permits the total contact area or footprint on a substrate to be less than that required when the chips are individually mounted on such a substrate or mother board. Additionally, the interconnections between the three integrated circuits take place internally of the chip carrier, reducing the exposed input/output contacts to only those required for connection to other components and circuits. In FIG. 2, only those input/output leads which terminate at a circle terminal, such as terminals 36, need to be connected to the external circuits. As shown in FIG. 2, there are only 40 such terminals (a reduction from 74 input/output terminals on the individual chips). In accordance with the present invention, the chip carrier not only provides internal connections of chips 30, 32 and 34, but additionally provides 40 input/output contacts to effectively accommodate the 40 terminals 36.

Integrated circuits 30, 32 and 34 are mounted in a dual cavity chip carrier 40 which will be described in detail herein with reference to FIGS. 3-13. As shown in FIG. 3, the chip carrier 40 is a multi-layer ceramic package mounted on a motherboard or a substrate 41. The chip carrier and the substrate are all constructed from ceramic material such as alumina ($Al_2O_3$). The chip carrier itself, in the embodiment of FIG. 3, employs six layers of ceramic material each having conductive or metallized patterns thereon. The six layers include layers 42, 44, 46, 48, 50 and 52. Layers 42 and 50 respectively serve as top and bottom annular seal rings to which metal lids 54 and 56 are secured to form hermetically sealed upper and lower cavities 58 and 60. An annular input/output layer 52 of a thickness greater than lid 56 serves as the bottom layer of the chip carrier. It is this bottom layer or input/output ring 52 to which both mechanical and electrical connection is made to a mother board or a substrate 41, such as by way of lead-tin solder connections 62. Each solder connection 62 electrically and mechanically connects the selected contact pad on the bottom surface of ring 52 with printed circuitry or the like located on the motherboard 41.

In this embodiment, it is contemplated that two integrated circuit chips may be mounted in the upper cavity 58 and one integrated circuit chip may be mounted in the lower cavity 60. As seen in FIG. 3, chip 32 is mounted in the upper cavity 58 on ceramic layer 46 (chip 34 is also located in this cavity but is not seen in FIG. 3). Chip 30 is mounted in the lower cavity 60 also to the common support layer 46. As is typical, integrated circuit chips such as chips 30 and 32 have two major surfaces of which one is typically coated with a metallized layer such as a gold alloy with that layer typically being intended to be connected to ground or to a B+ voltage supply by way of a circuit connection. The other major surface is typically provided with an array of contact pads, such as pads 64 on chip 32 in FIG. 3, and these serve as input/output terminals for connecting the integrated circuits with other circuits. As shown in FIG. 3, chips 30 and 32 are mounted on opposing surfaces of layer 46 so that the metallized major surface of each chip is in abutting flat contact with layer 46 and the input/output contact pads 64 located on the other major surface faces away from layer 46. As will be seen hereinafter, layer 46 is provided on its oppositely facing major surfaces with large metallized mounting pads to accommodate and make electrical as well as mechanical contact with the metallized surface on the back side of each chip.

The input/output contact pads 64 on chips 30 and 32 are interconnected with metallized patterns 66, located on the various ceramic layers, by way of suitable wire bonds 68. These wire bonds are typically gold wires approximately 0.001 inch in diameter (1 mil). Some of these metallized patterns 66 on the ceramic layers extend laterally along the surface of the layer and make mechanical and electrical contact with one or more vertically extending vias 70. These vias are metallized vertically extending columns of conductive material which extend through the various ceramic layers 44, 46 and 48 to interconnect with various of the metallized laterally extending patterns thereon. Additionally, some of the laterally extending metallized patterns 66 extend to the peripheral edge of the carrier and make contact with a vertically extending metallized groove or castellation 72. These castellations 72 extend downwardly in a vertical direction and each makes contact with an input/output contact pad 74 located on the bottom of the carrier on the input/output contact ring 52. It is to these input/output contacts 74 that both mechanical and electrical connection is made to the mother board 41 by way of the lead-tin solder connections 62.

The ceramic layers 42-52 may all be formed from green or uncured ceramic material, essentially of alumina (Al₂O₃). This material is typically furnished in sheets and they are shaped by pressing, molding and punching to conform to the configurations as seen in the drawings herein. The metallized or conductive patterns, such as patterns 66 in FIG. 3, may typically be produced by deposition procedures using masking or screening techniques to apply successive layers of suitable materials, such as a layer of tungsten applied directly to the ceramic material. These are covered with a layer of nickel and finally a layer of gold, both of which are plated layers. The vertical vias 70 in FIG. 3 are formed by making vertical holes through the ceramic layers where they interconnect with internal terminals on the metallized layers 66. The holes are then filled with a metallic paste which converts to a solid electrically conductive form. Lids 54 and 56 are metallic and they make contact with their respective seal rings 42 and 50. The bonding between the two layers may be obtained from a gold-tin preform, which when heated on the order of 300° C., forms a hermetic seal so that the integrated circuit chips and their wire bondings are located in protected environments within the respective cavities 58 and 60.

Attention is now directed to FIGS. 4-7 which illustrate the composite chip carrier but without chips mounted thereon and with the lids 54 and 56 removed. FIG. 4 is a plan view looking downward at the top of the chip carrier with the lid being removed exposing cavity 58. Annular seal ring 42 surrounding the cavity has its upper surface coated with a metallized seal ring pattern 80 to which lid 54 is sealed during assembly. Inwardly of the seal ring 42 there is exposed the upper surface of ceramic layer 44 without the metallized patterns being illustrated (these are illustrated and described hereinafter with reference to FIG. 8). An inverted, somewhat T-shaped opening 82 is formed in layer 44 exposing an inverted T-shaped contact pad 84 located on the upper surface of ceramic layer 46. It is on this contact pad 84 to which chips 32 and 34 are electrically and mechanically mounted within cavity 58.

Figure 5:
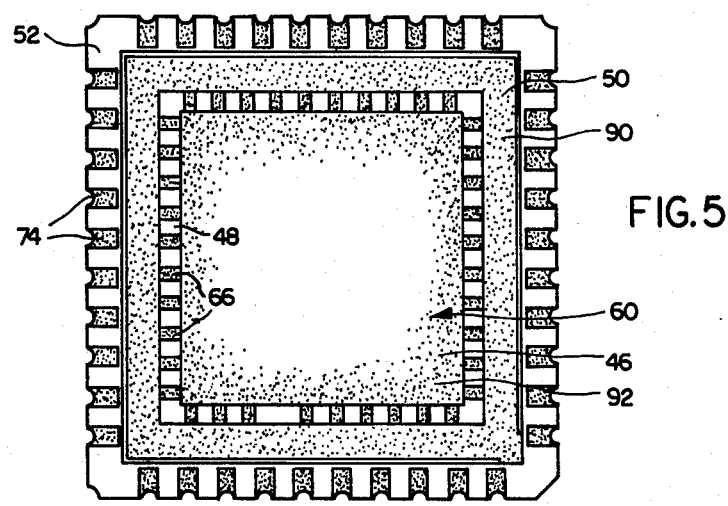
FIG. 5 is a bottom view, with the bottom lid removed, of the chip carrier.

Attention is specifically directed to FIG. 5 which illustrates the bottom of the carrier with bottom lid 56 removed exposing cavity 60 but with chip 30 removed. This view more specifically illustrates the metallized input/output contact pads 74 located on the bottom surface of the input/output ring 52. As seen then, there are ten input/output contact pads adjacent each peripheral edge of the carrier for a total of 40 input/output contact pads. Each of the contact pads 74 is in electrical communication with a castellation 72 formed in the peripheral side edges. Each castellation extends from the bottom surface of the carrier vertically upward through layer 44. The annular seal ring 50 is also exposed in FIG. 5 and is located just inwardly from layer 52. This is covered with an annular metallized pattern 90 to which lid 56 will be secured as by bonding the materials together with a gold-tin preform which when heated, on the order of 300° C., forms a hermetic seal so that chip 30 and its wire bondings are located in a protected environment within cavity 60.

Also in FIG. 5, there is exposed a portion of layer 48 having metallized patterns 66 thereon and which will become more apparent hereinafter with reference to FIG. 11. Lastly, the center portion of FIG. 5 represents the floor of cavity 60 and which is located on the bottom surface of ceramic layer 46. The area visible in FIG. 5 is preferably coated with a metallized layer 92 serving as an enlarged contact pad to which the integrated circuit chip 30 is electrically and mechanically mounted.

Figure 6:
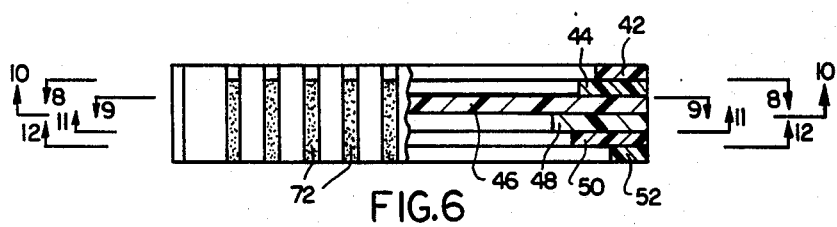
FIG. 6 is a view taken along line 6—6 in FIG. 4 looking in the direction of the arrows.
Figure 7:
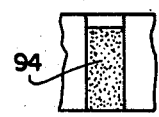
FIG. 7 is a fragmentary view taken generally along line 7—7 looking in the direction of the arrows in FIG. 4.

FIG. 6 provides an illustration of the castellation 72 around the peripheral edge of the carrier. It is to be noted that each castellation 72 extends vertically downward along the edges of layers 44-52. FIG. 7 illustrates an edge metallization 94 which extends on a canted corner vertically along layers 44-52. As will be seen hereinafter, this metallization 94 provides an electrical tie between the seal ring conductive patterns 80 and 90.

Attention is now directed to FIGS. 8-13 which illustrate the configurations of the ceramic layers 44, 46, 48 and 50 as well as the metallized patterns thereon.

Figure 8:
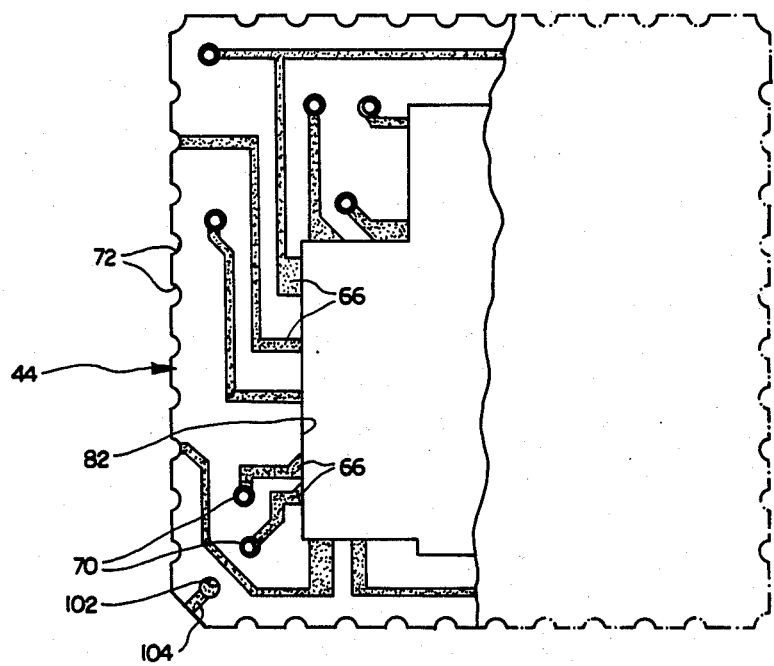
FIG. 8 is a view taken generally along line 8—8 looking in the direction of the arrows in FIG. 6.

Reference is now made to FIG. 8 which illustrates the upper surface of ceramic layer 44. This layer has an inverted T-shaped aperture 82 formed therein of a size corresponding with that of the mounting pad 84 on the upper surface of ceramic layer 46. As seen in FIG. 8, a plurality of conductive patterns 66 extend from aperture 82 laterally along the surface of layer 44. Some of the patterns extend to the peripheral edge castellations 72 and others extend to and terminate at vertical vias 70. The vertical vias 70 interconnect with other metallized layers 66 on other ceramic layers of the chip carrier. At the bottom lefthand corner in FIG. 8 there is shown a landing area 102 at which a vertically conductive via terminates after extending downwardly through the seal ring 42. A metallized conductive segment 104 connects this landing area 102 with the edge metallization 94 (see FIG. 7) which permits electrical connection between the two seal rings.

Figure 9:
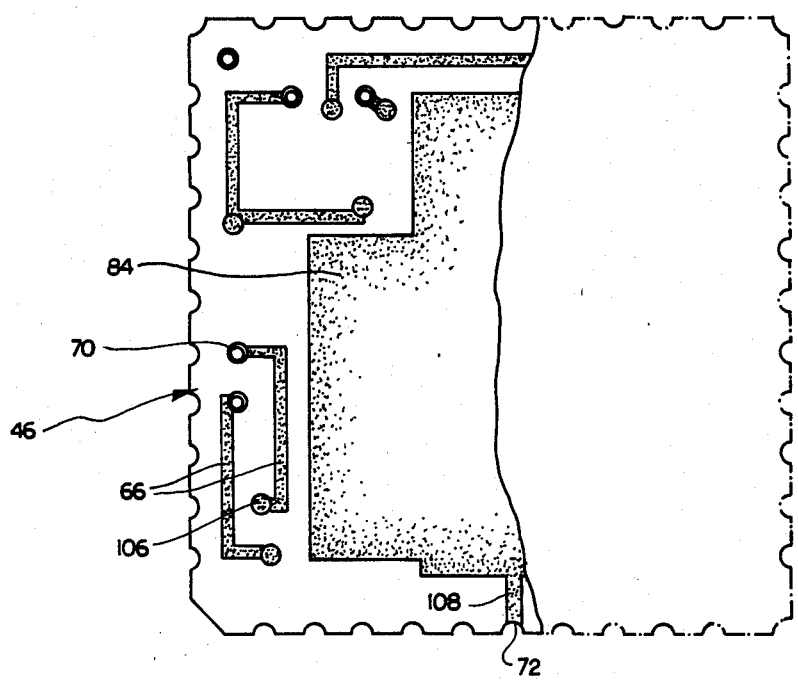
FIG. 9 is a view taken generally along line 9—9 looking in the direction of the arrows in FIG. 6.

FIG. 9, in a manner similar to that of FIG. 8, illustrates the metallized patterns on the upper surface of ceramic layer 46. This is a solid layer and includes an enlarged inverted T-shaped metallized pattern serving as the mounting pad 84. Additional metallized patterns 66 on layer 46 extend to landing areas 106 for vertical vias which extend through layer 44 but terminate at layer 46. Some patterns also contact vertical vias 70 which extend through layer 46 to the next layer in this ceramic package. Some of these conductive patterns are in electrical connection with the mounting pad 84 and extend either to such landing areas or to such vertical vias. Additionally, a conductive path 108 extends from the mounting pad 84 to an edge castellation 72.

Figure 10:
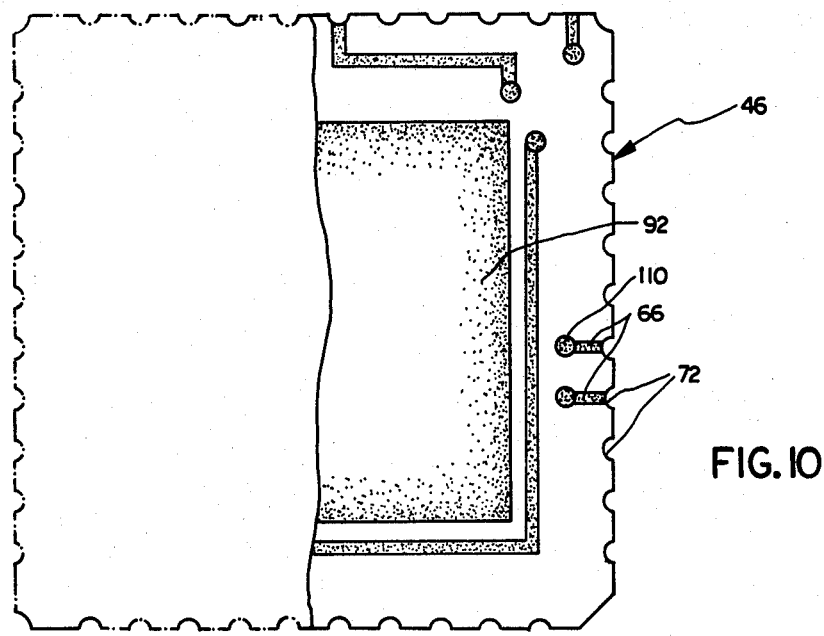
FIG. 10 is a view taken generally along line 10—10 looking in the direction of the arrows in FIG. 6.

Reference is now made to FIG. 10 which illustrates the metallized patterns on the bottom surface of ceramic layer 46 including the lower mounting pad 92 onto which chip 30 is mechanically and electrically mounted. Some of the conductive patterns 66 extend from landing areas 110 to edge castellations 72. These landing areas 110 are for vertical vias which extend through layer 46.

Figure 11:
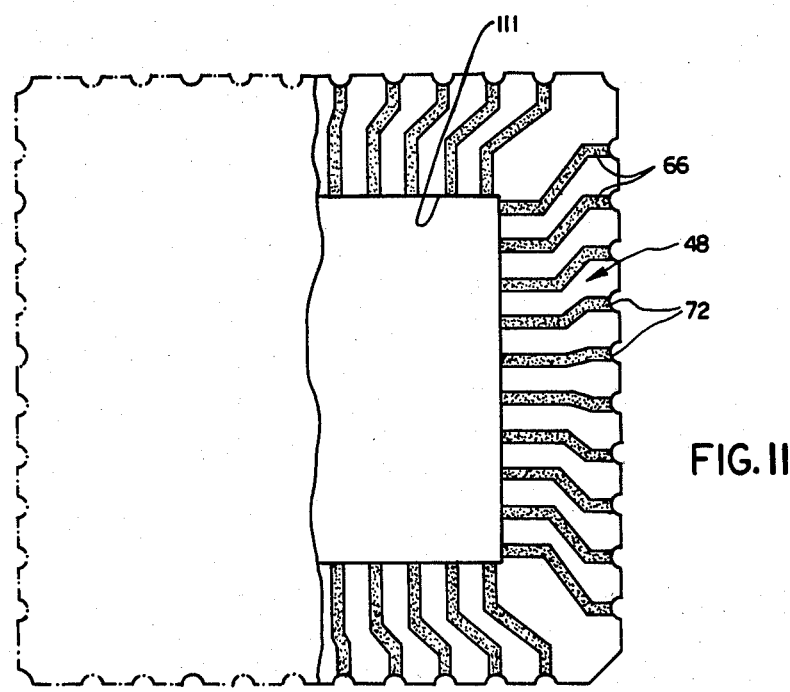
FIG. 11 is a view taken generally along line 11—11 looking in the direction of the arrows in FIG. 6.

Reference is now made to FIG. 11 which shows the metallized patterns 66 on the bottom surface of ceramic layer 48. This is an annular layer with a rectangular aperture located at the center. This aperture 111 is of sufficient size that it corresponds essentially with that of mounting pad 92 on the bottom surface of ceramic layer 46 and is of sufficient size to permit insertion of chip 30 into the cavity so that it may be mounted on mounting pad 92. The conductive patterns 66 extend from points adjacent to aperture 111 and extend to the edge castellation 72 as is shown in FIG. 11. It is contemplated that wire bonding will interconnect contact pads on the exposed surface of chip 30 with individual ones of the metallized patterns 66.

Figure 12:
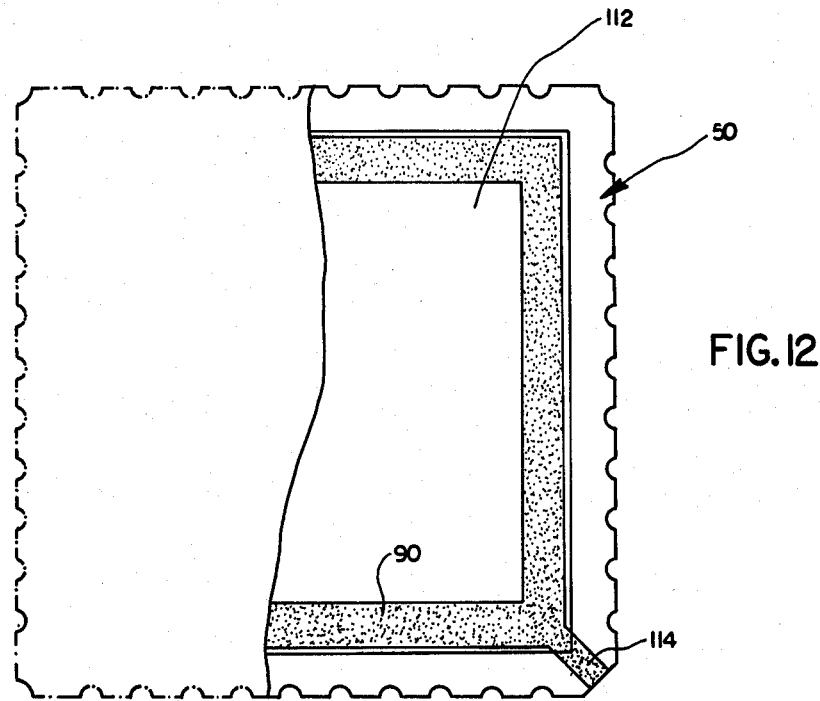
FIG. 12 is a view taken generally along line 12—12 looking in the direction of the arrows in FIG. 6.

Reference is now made to FIG. 12 which illustrates the bottom surface of ceramic layer 50. This layer has a square aperture 112 at its center corresponding essentially with that of aperture 111 in layer 48 to permit insertion of chip 30 into the cavity for mounting on the mounting pad 92 on layer 46. This view also exposes the metallized pattern 90 on layer 50 which, as discussed herebefore, serves as a seal ring to which lid 56 is hermetically sealed. A conductive segment 114 extends from the conductive pattern 90 to the canted edge of the carrier at which it makes electrical contact with the edge metallization 94 (see FIG. 7). This connects with a similar conductive portion 104 (see FIG. 8) and then by way of a via through layer 42 provides an electrical path connecting these seal rings together.

Figure 13:
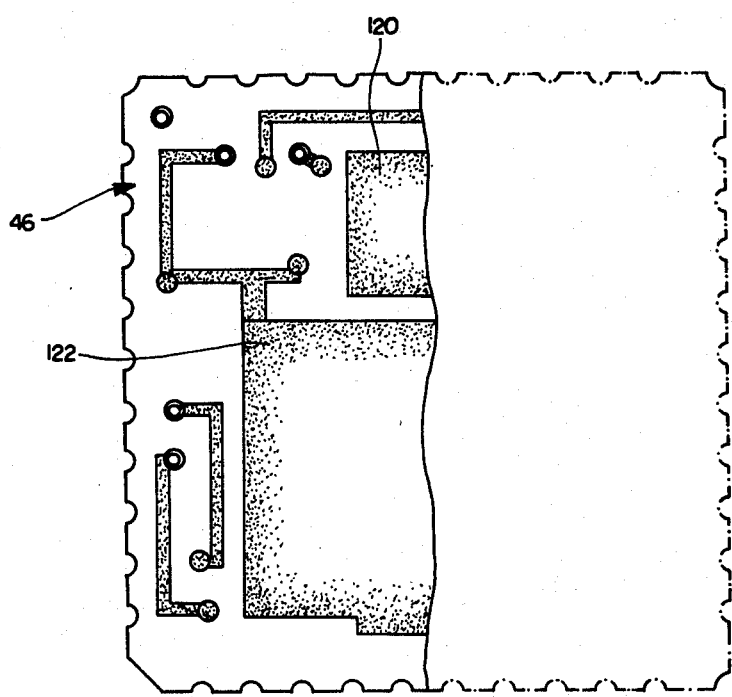
FIG. 13 is a view similar to that of FIG. 8 and serves as an alternative embodiment for that layer of the chip carrier.

Reference is now made to FIG. 13 which is similar to that of FIG. 9 and illustrates a different embodiment of the metallized pattern used on the top surface of layer 46. In this embodiment, the inverted T-shaped contact pad 84 of FIG. 9 is replaced with two separate enlarged square shaped contact pads 120 and 122 which are electrically and mechanically separated from each other. This permits mounting chips on pads 120 and 122 wherein the back metallizations are intended to be tied to different potentials, such as one being tied to a ground potential and the other being tied to a B+ potential. Consequently, then, with this embodiment, the two integrated circuits to be placed and mounted within cavity 58 may be connected to either a high or low voltage level and interfaced to the memory chip 30 through the metallized patterns and vias within the carrier.

Although the invention has been described in conjunction with a preferred embodiment, it is to be appreciated that various modifications and arrangements may be made without departing from the spirit and scope of the invention as defined by the appended claims.

What is claimed is:

1. An implantable pulse generator comprising:
   a human implantable sealed housing of biocompatible material, a power supply and a pulse generator circuit mounted within said housing with said circuit being powered by said supply for supplying pulses, said curcuit including at least first and second integrated semiconductor chips, a single printed circuit mother board for carrying said chips, and chip carrier means mounted on said mother board and carrying said semiconductor chips, said chip carrier means including:
   a unitized body comprised of a plurality of ceramic layers fused together, said body having oppositely facing major surfaces, a cavity disposed in a first of said major surfaces, said first and second chips being mounted in said cavity, and a lid member covering and sealing said cavity so as to hermetically seal said chips therein.

2. An implantable pulse generator as set forth in claim 1, wherein said cavity has a floor on one of said layers, said floor having metallized patterns thereon including metallized mounting pad areas electrically and mechanically mounting said chips.

3. An implantable pulse generator as set forth in claim 2, including a pattern of metallized vertical vias extending through various of said ceramic layers.

4. An implantable pulse generator as set forth in claim 3, wherein each said layer has a network of laterally extending metallized patterns thereon, some of said patterns making electrical contact with a said via to thereby electrically interconnect patterns on different layers.

5. An implantable pulse generator as set forth in claim 4, wherein said chips have an array of input/output contact pads thereon, and wire bonding connecting some of said input/output pads with some of said metallized patterns on one of said ceramic layers, whereby some of said input/output contact pads on one of said chips are interconnected with some of said input/output contact pads on the other of said chips by means of said metallized patterns on said layers and by said vias and said wire bonding.

6. An implantable pulse generator as set forth in claim 5 including a pattern of spaced apart metallized castellations on the peripheral edges of said carrier, said castellations extending vertically from the bottom surface of said carrier through a plurality of said layers so as to interconnect with metallized patterns on some of said layers as they extend laterally to and connect with various of said edge castellations.

7. An implantable pulse generator as set forth in claim 6, including a plurality of input/output contact pads located on the bottom surface of said carrier with each said input/output contact pad being in electrical connection with one of said edge castellations.

8. An implantable pulse generator as set forth in claim 7, wherein said pulse generator circuit includes a third semiconductor chip, and wherein a second cavity is disposed in a second of said major surfaces, said third chip being mounted in said second cavity, and a second lid member covering and hermetically sealing said second cavity so as to hermetically seal said third chip therein.

9. An implantable pulse generator as set forth in claim 8, wherein said second cavity has a floor on one of said ceramic layers with said floor having a metallized pattern thereon defining at least one mounting pad area electrically and mechanically mounting said third chip.

10. An implantable pulse generator as set forth in claim 9 wherein said ceramic layer having said floor in said second cavity is the same ceramic lyaer having a floor for the first of said cavities, said layer serving as a common mounting layer for the integrated circuit chips located in both of said cavities.

11. An implantable pulse generator as set forth in claim 10, wherein the uppermost layer of said carrier is an annular seal ring having an annular metallized pattern on its upper surface to which the upper lid is secured, a bottom annular seal ring having an annular conductive pattern thereon to which the bottom lid is secured, and a metallized pattern extending vertically along a peripheral edge of said carrier electrically interconnecting said annular metallized patterns on said bottom and upper seal rings.

* * * * *